US010169882B1

(12) United States Patent
Tokunaga et al.

(10) Patent No.: US 10,169,882 B1
(45) Date of Patent: Jan. 1, 2019

(54) OBJECT SIZE DETECTION WITH MOBILE DEVICE CAPTURED PHOTO

(71) Applicant: WinguMD, Inc., Half Moon Bay, CA (US)

(72) Inventors: Manabu Tokunaga, Half Moon Bay, CA (US); Jonathan Harman, Pacifica, CA (US)

(73) Assignee: WinguMD, Inc., Half Moon Bay, CA (US)

( * ) Notice: Subject to any disclaimer, the term of this patent is extended or adjusted under 35 U.S.C. 154(b) by 224 days.

(21) Appl. No.: 15/189,926

(22) Filed: Jun. 22, 2016

Related U.S. Application Data

(60) Provisional application No. 62/217,511, filed on Sep. 11, 2015.

(51) Int. Cl.
  *G06T 7/60* (2017.01)
  *G06T 7/00* (2017.01)
  (Continued)

(52) U.S. Cl.
  CPC .............. *G06T 7/60* (2013.01); *A61B 5/0013* (2013.01); *A61B 5/0022* (2013.01);
  (Continued)

(58) Field of Classification Search
  CPC ...................... G06T 7/60; G06T 7/0085; G06T 2207/30204; A61B 5/0013; A61B 5/0022;
  (Continued)

(56) References Cited

U.S. PATENT DOCUMENTS

| 8,150,494 B2 | 4/2012 | Simon et al. |
| 8,422,777 B2 | 4/2013 | Aller |

(Continued)

OTHER PUBLICATIONS

Li et al., "A novel method and workflow for stereotactic surgery with a mobile intraoperative CT imaging device." SPIE Medical Imaging. International Society for Optics and Photonics, 2015, pp. 94151V-1-94151V-7.

(Continued)

*Primary Examiner* — Michael E Teitelbaum
(74) *Attorney, Agent, or Firm* — Haynes Beffel & Wolfeld LLP

(57) ABSTRACT

Roughly described, a method for estimating a size measurement of a subject feature on a body, for use with a photo, snapped by a camera which may be handheld. A reference marker is placed on the body near the subject feature. The reference marker includes concentric rings to help confirm its identify, and registration markings to determine the pose at which the photo was taken. The registration markings can be dots at vertices of a square. The method can include detecting concentric ellipses in the photo corresponding to the concentric circles, detecting the registration markings in the photo within a predetermined region which is outside the detected ellipses, geometrically transforming at least the subject feature in the photo based on the detected locations of the registration markings, calculating the scale of the photo based on the detected registration markings, and providing the transformed image and scale for the size measurement.

19 Claims, 12 Drawing Sheets

(51) Int. Cl.
*G06K 9/46* (2006.01)
*A61B 5/00* (2006.01)
*A61B 5/107* (2006.01)

(52) U.S. Cl.
CPC .......... *A61B 5/0077* (2013.01); *A61B 5/1075* (2013.01); *A61B 5/1079* (2013.01); *A61B 5/6898* (2013.01); *G06K 9/4604* (2013.01); *G06T 7/0085* (2013.01); *G06T 2207/30204* (2013.01)

(58) Field of Classification Search
CPC ... A61B 5/0077; A61B 5/1075; A61B 5/1079; A61B 5/6898; G06K 9/4604
See application file for complete search history.

(56) References Cited

U.S. PATENT DOCUMENTS

| | | | |
|---|---|---|---|
| 9,223,932 B1 | 12/2015 | Rice et al. | |
| 9,594,980 B1* | 3/2017 | Graham | H04N 5/23222 |
| 2002/0164077 A1* | 11/2002 | Lee | G06K 9/4604 382/224 |
| 2004/0093011 A1* | 5/2004 | Vrba | A61B 5/1076 606/200 |
| 2006/0210132 A1* | 9/2006 | Christiansen, II | A61B 5/0059 382/128 |

OTHER PUBLICATIONS

Ferreira, Tiago et al., "ImageJ user guide." IJ1. 46r. Natl. Inst. Health, Bethesda, MD. http://rsb. info. nih. gov/ij/ docs/guide/user-guide. pdf (2012), 198 pages.
Burger et al., Digital image processing: an algorithmic introduction using Java, Chapter 21 Geometric Operations, Springer, 2016, pp. 513-538.
Eberly, "Perspective Mappings," Geometric Tools, LLC (2012), available at geometrictools.com/Documentation/PerspectiveMappings.pdf, Aug. 16, 2011 (last modified Nov. 3, 2012), pp. 1-10.
Behring, et al., "Optical coordinate measuring techniques for the determination and visualization of 3D displacements in crash investigations". No. 2003-01-0891, SAE Technical Paper, 2003, 7 pages.
DICOM PS3.1 2015c—Introduction and Overview, 2015 NEMA, 34 pages.
DICOM PS3.2 2015c—Conformance, 2015 NEMA, 322 pages.
DICOM PS3.3 2015c—Information Object Definitions, 2015 NEMA, 1338 pages.
DICOM PS3.4 2015c—Service Class Specifications, 2015 NEMA, 404 pages.
DICOM PS3.5 2015c—Data Structures and Encoding, 2015 NEMA, 138 pages.
DICOM PS3.6 2015c—Data Dictionary, 2015 NEMA, 204 pages.
DICOM PS3.7 2015c—Message Exchange, 2015 NEMA, 128 pages.
DICOM PS3.8 2015c—Network Communication Support for Message Exchange, 2015 NEMA, 72 pages.
DICOM PS3.10 2015c—Media Storage and File Format for Media Interchange, 2015 NEMA, 48 pages.
DICOM PS3.11 2015c—Media Storage Application Profiles, 2015 NEMA, 96 pages.
DICOM PS3.12 2015c—Media Formats and Physical Media for Media Interchange, 2015 NEMA, 92 pages.
DICOM PS3.14 2015c—Grayscale Standard Display Function, 2015 NEMA, 66 pages.
DICOM PS3.15 2015c—Security and System Management Profiles, 2015 NEMA, 142 pages.
DICOM PS3.16 2015c—Content Mapping Resource, 2015 NEMA, 1150 pages.
DICOM PS3.17 2015c—Explanatory Information, 2015 NEMA, 692 pages.
DICOM PS3.18 2015c—Web Services, 2015 NEMA, 138 pages.
DICOM PS3.19 2015c—Application Hosting, 2015 NEMA, 96 pages.
DICOM PS3.20 2015c—Image Reports using HL7 Clinical Document Architecture , 2015 NEMA, 152 pages.

* cited by examiner

OBJECT SIZE DETECTION WITH MOBILE DEVICE CAPTURED PHOTO

CROSS-REFERENCE TO OTHER APPLICATIONS

Applicants hereby claim the benefit under 35 U.S.C. 119(e) of U.S. Provisional Application No. 62/217,511, filed 11 Sep. 2015, by Manabu Tokunaga, Jonathan Harman and Oliver Aalami and entitled "OBJECT SIZE DETECTION AND PHOTOGRAPHIC COLOR CORRECTION SYSTEM WITH MOBILE DEVICE CAPTURED PHOTO." The provisional application is hereby incorporated by reference herein.

BACKGROUND

Field of the Invention

An object size detection system for estimating the actual size of objects from photos taken with a mobile or hand-held camera. The system can be used for accurately documenting and comparing changes of external surface features (physical findings), either on human subjects, animals, or inanimate objects (e.g., a car).

Description of the Related Art

In the field of medicine, it is often desirable to determine the size of surface features on a patient's body. For example, if the size of a lesion on the patient's skin is decreasing over time, this may indicate that it is healing. If it is increasing, then this may indicate that it is getting worse. In a clinical setting, a trained physician or clinician can measure the feature directly. But it is not always desirable to require the patient to come to a clinic for the measurement. It may be inconvenient or expensive for the patient to do so, and in some cases the patient may be located very far away. In the developing field of Distance Medicine, for example, the patient and the clinician may be on opposite sides of the world. Sometimes it is possible for the patient to measure the feature, but it is usually safer and more accurate to have it measured by a trained physician or clinician.

Recently, a new field has arisen which might be called Mobile Medical Collaboration. The idea is to permit patients themselves to use a mobile phone or other handheld device to send medically meaningful images to a physician or clinician, who can then diagnose a condition or evaluate its progress from a distance. If this can be accomplished, then tasks such as the measurement of the size of surface features on the patient's body can be performed without requiring the patient to travel to the clinician, or vice versa. Thus in recent years, the use of photography to document medical conditions has become important, especially with cameras that are embedded in mobile electronic devices including cellular phones and electronic tablets.

A problem arises, though, because the photographs are taken freehand. With a freehand photo, there is no assurance that the photo was taken from a known distance to the feature, or at the correct angle from the feature. If the distance is not known, then typically neither is the scale of the image known. The clinician viewing the photograph is not able to accurately determine the size of the feature, since the size in the photograph differs depending on the distance that the camera was located away from the feature when the photo was snapped. Also, if the camera was located at an angle from the surface plane of the feature, then the version of the feature observable in the photograph will be distorted as compared to the actual feature on the patient's body.

One solution to this problem is to provide a mounting device that holds the camera with fixed, rigid geometry to the patient's body. This solution is often unworkable, though, because the mounting device may be costly or difficult for an untrained person to operate, or because it simply may not be available where the patient is located. Another solution does not require fixed geometry, but rather uses sonar or a laser to detect the distance of the camera to the subject feature. But this too is expensive and requires specialized equipment. It is also known to apply fiducial markers to a patient's body for stereotactic localization for radiographic imaging and during surgery. Again, expensive and specialized equipment is needed for this solution, which does not lend itself for use in mobile medical collaboration.

Accordingly, a need has arisen for better, less costly, and more easily available ways to image a subject feature on a body which will permit accurate size measurements.

SUMMARY

Roughly described, the invention involves a method for estimating a size measurement of a subject feature on a body, for use with a photo, snapped by a camera. The camera can be handheld since it need not be located or oriented at any precise position relative to the subject feature. The photo contains both the subject feature and a reference marker which includes two components: location markings and registration markings. The location markings are used to help ensure that the system has properly located the reference marker, and also to provide an anchor based on which to search for the registration markings. The registration markings are then used to determine and correct for the pose at which the photo was taken. Preferably the location markings include at least two concentric rings, and the registration markings are markings which identify the vertices of a regular polygon having at least four sides (preferably a square).

The method includes detecting in the captured photo a group of concentric ellipses corresponding to the group of concentric circles in the reference marker, detecting the registration markings in the captured photo within a predetermined region which is outside the concentric ellipses detected in the captured photo, geometrically transforming at least the subject feature in the photo in dependence upon the locations in the captured photo of at least first, second, third and fourth vertices of the polygon as identified by the registration markings, and providing the transformed image for the size measurement. In an embodiment the location of two of the registration markings can also be used to calculate the scale of the photo to be provided for the size measurement in association with the transformed image.

The above summary of the invention is provided in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description that is presented later. Particular aspects of the invention are described in the claims, specification and drawings.

BRIEF DESCRIPTION OF THE DRAWINGS

The invention will be described with respect to specific embodiments thereof, and reference will be made to the drawings, in which.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Figure 1:
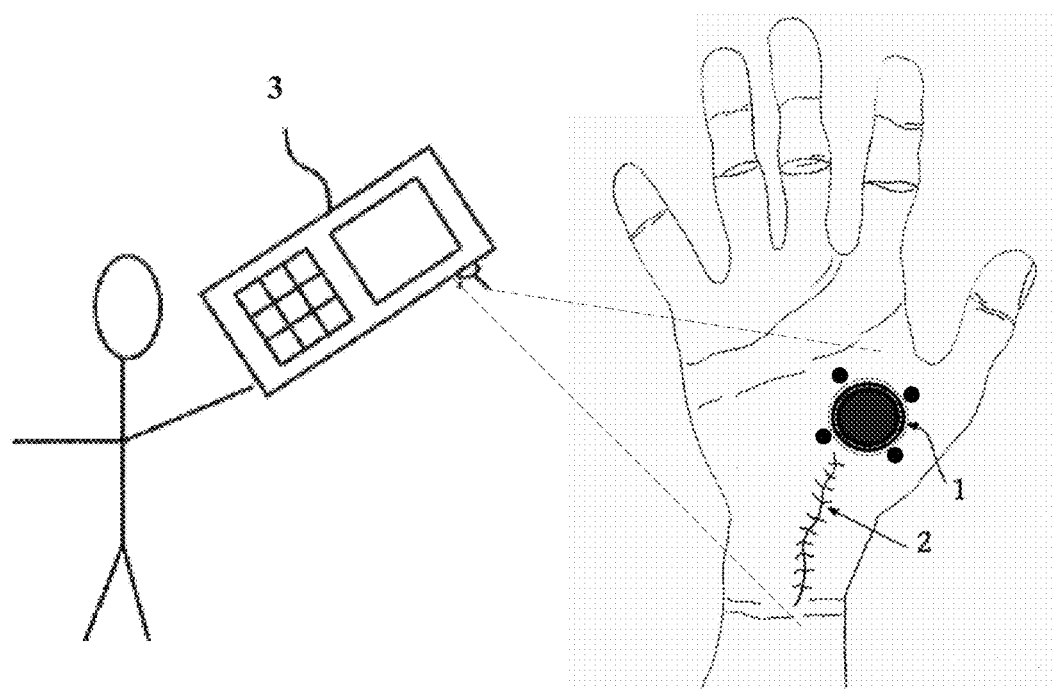
FIG. 1 illustrates the general context of a system according to an embodiment of the invention.

FIG. 1 illustrates the general operation of a system according to an embodiment of the invention. The drawings herein are not necessarily drawn to scale. In the embodiment of FIG. 1, a subject feature 2, in this case a suture, is present on a patient's hand. It is desired to be able to measure the length of the suture. In order to accomplish this, a reference marker 1 is placed on the patient's hand, preferably close to the subject feature, and generally in the same plane as the feature. The patient or another person, who need not be trained, snaps a photograph containing both the reference marker 1 and the subject feature 2, using a handheld device 3, such as a cell phone camera. Software or hardware either on the cell phone 3 or running on a separate processor (not shown) to which the photograph is transmitted, uses the reference marker 1 as captured in the photograph in order to correct the photograph for perspective and to determine the scale of the image. With this information, a clinician at a different location can easily determine the length of the subject feature 2.

In one embodiment, the reference marker 1 is printed on a sticker that the patient can apply. In another embodiment, the reference is printed on a re-usable card that rests on the patient's hand. Optionally, the card may have a handle portion (not shown) to help hold the reference marker in place during photography.

Figure 2:
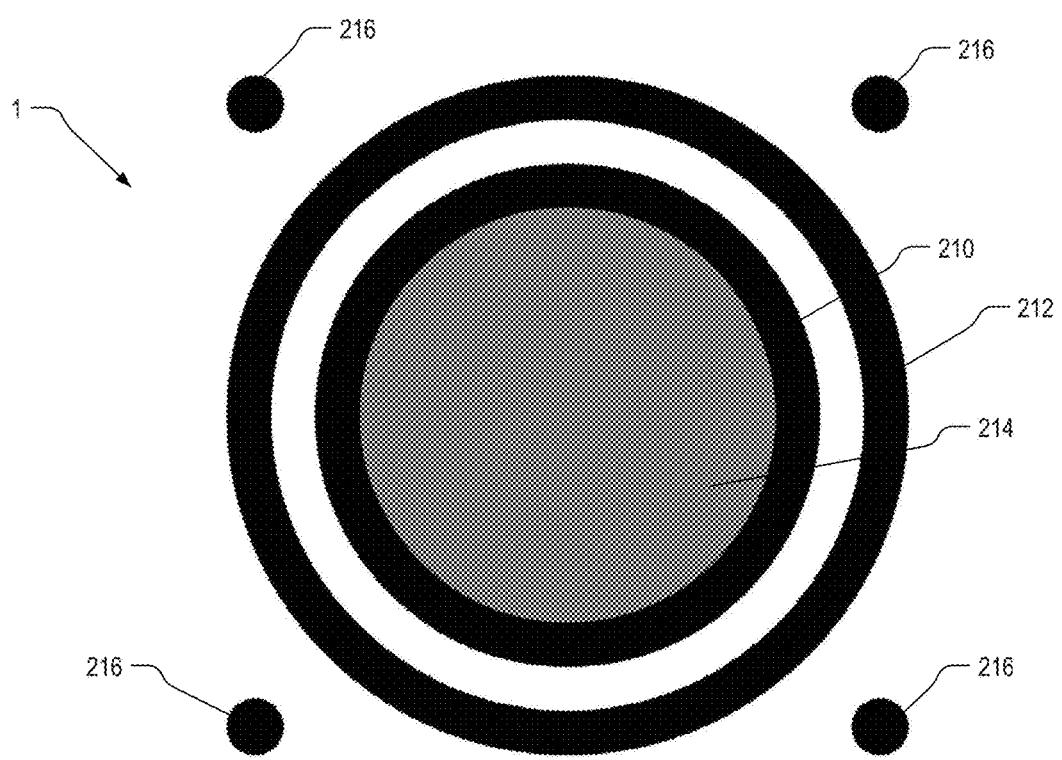
FIG. 2 is an enlarged illustration of the reference marker of FIG. 1.

FIG. 2 is an enlarged illustration of the reference marker 1 of FIG. 1. It has two components: location markings and registration markings. The location markings are used to help ensure that the system has properly located the reference marker, and the registration markings are then used to determine and correct for the pose at which the photo was taken. The location marking includes two concentric circular rings 210 and 212, the ring 212 being an outer ring. Inside the ring 210 is solid colored fill 214 which may be used for color correction. The registration markings are located outside the outer ring 212 and include four circular dots 216. Other shapes besides circular dots can be used in different embodiments, so long as they can be used to identify the vertices of a regular polygon.

The polygon identified by the four dots 216 in FIG. 2 is a square, though in other embodiments it can be a pentagon, hexagon, or another regular polygon. Only a square is needed (four vertices), but additional vertices may help improve accuracy. In addition, the registration markings can use any detectable means to identify the vertices of the polygon. In FIG. 2, for example, each circular dot 216 identifies a vertex located at its center point. Other embodiments can use other means, such as arrows terminating at the vertices, lines recognizable as portions of sides of the polygon, and so on.

Though concentric rings are preferred for the location markings, another embodiment instead can use other concentric regular polygons. In some embodiments these concentric polygons do not need to have the same angle of rotation as each other, nor need they necessarily even have the same number of sides as each other. If the polygons have many sides, then with appropriate allowances in the detection mechanism, their edges can be detected as circles (ellipses in the captured photo). As used herein, in fact, a polygon with an infinite number of sides is considered herein to be a circle. Alternatively or additionally, the detection mechanism can be adapted in order to detect the actual shapes used. Whichever type of location markings are used, they have an outer boundary in the captured photo. A search region is determined for the registration markings relative to this outer boundary, the search region being outside the outer boundary but within some predetermined region relative to such outer boundary. The registration markings are then detected by searching within the search region.

Figure 3:
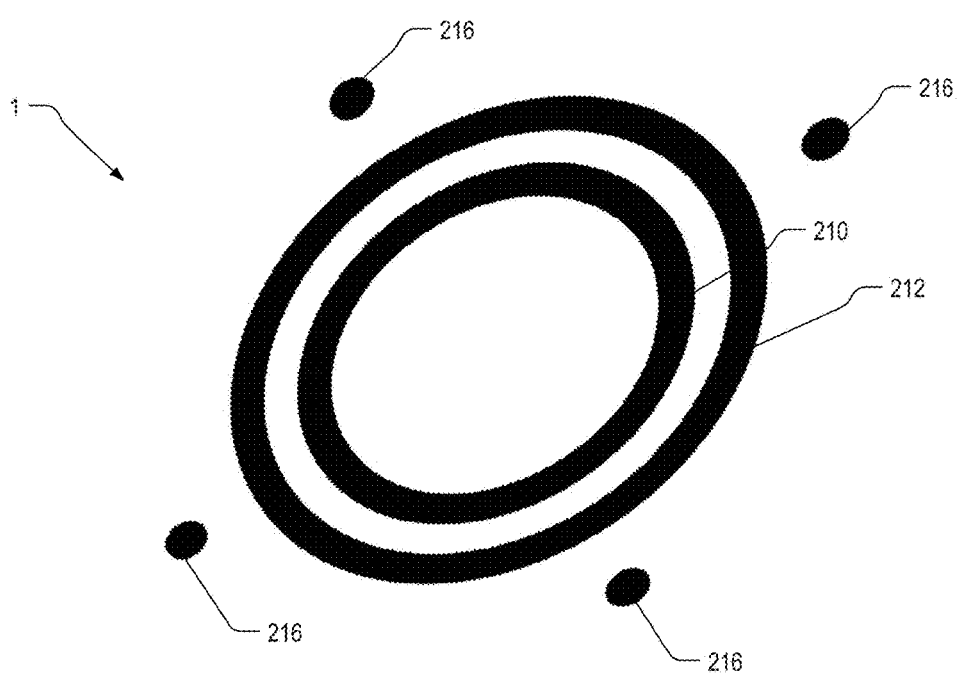
FIG. 3 is an illustration of the reference marker of FIG. 1, as it might appear in a captured photograph.

FIG. 3 is an illustration of the reference marker 1, as it might appear in a captured photograph which was taken at an angle. It can be seen that the concentric rings 210 and 212 now appear elliptical, as do the four registration markings 216. The four registration markings 216 also are skewed, and potentially keystoned, relative to a square. The rings 212 and 213 may not appear precisely elliptical, for example due to keystoning, but so long as the camera was oriented relatively perpendicularly relative to the reference marker, they will be close to elliptical. Notably, circles are preferably used for the location markings rather than some other shape, because circles are rotationally agnostic. Circles will appear in the captured photograph as ring-like objects that are very close to elliptical, regardless of the orientation of the camera when the photograph is taken—assuming the camera angle is not far off of perpendicular.

Figure 4:
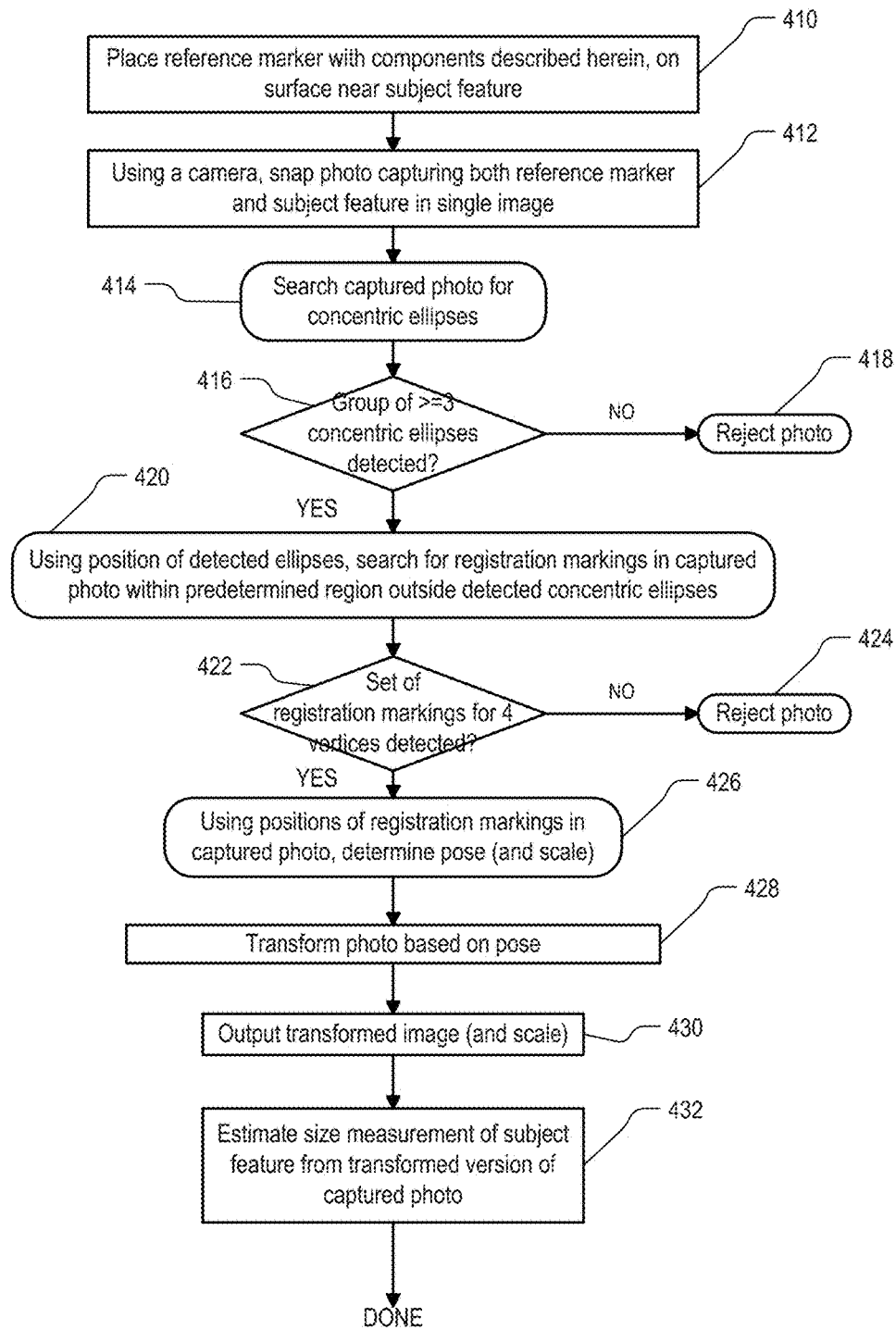
FIGS. 4, 5, 8 and 9 are flowcharts illustrating steps that might be used to implement the invention.

FIG. 4 is a flowchart illustrating steps that might be used to implement the invention. As with all flowcharts herein, it will be appreciated that many of the steps can be combined, performed in parallel or performed in a different sequence without affecting the functions achieved. In some cases, as the reader will appreciate, a re-arrangement of steps will achieve the same results only if certain other changes are made as well. In other cases, as the reader will appreciate, a re-arrangement of steps will achieve the same results only if certain conditions are satisfied. Furthermore, it will be appreciated that the flow charts herein show only steps that are pertinent to an understanding of the invention, and it will be understood that in a specific embodiment, numerous additional steps for accomplishing other functions for that embodiment can be performed before, after and between those steps shown.

Referring to FIG. 4, in broad overview, after snapping the photograph, the system performs steps for detecting location markings in the captured photograph, the location markings being the concentric circles of the reference marker, then using the detected position of the location markings to find the registration markings, such as the four dots 216. Then the photo is transformed such that the four dots once again form a square, a transformation which also transforms the subject feature 2. The positions of the registration markings 216 also determine the scale of the photograph. The system then outputs the transformed image, in association with an indication of the scale, and this is sufficient for a user or a computer system to take the desired measurement of the subject feature.

In an embodiment of the invention, many of the individual image processing functions that are performed make use of functions available in the ImageJ program developed at the National Institutes of Health. ImageJ is a public domain program which can display, edit, analyze, process, save and print images. ImageJ is described for example in Ferreira & Rasband, ImageJ user guide, IJ 1.46r (2012), imagej(dot)nih(dot)gov/ij/docs/guide/user-guide.pdf, visited 2016-04-22, incorporated by reference herein.

Referring to FIG. 4, in step 410, the reference marker 1 of FIG. 2 is placed on the subject surface, preferably near the subject feature. Proximity to the subject feature is desired both because the reference marker is then more likely to be nearly coplanar with the subject feature, and also because the captured photograph in the embodiment of FIG. 4 is to contain both the reference marker 1 and the subject feature 2 in a single photograph. The subject surface is located on a "body". In one embodiment the "body" is literally a human body. In other embodiments, however, the "body" can be any solid object, such as an automobile. Additionally, the system works best when the reference marker is placed so as to share a common plane with the subject feature. The accuracy of the measurement can still be excellent if not, but will diminish by the extent by which one or the other of the subject feature and the reference marker deviate from planarity and/or coplanarity.

In step 412, using the camera, a photo is snapped capturing both the reference marker 1 and the subject feature 2. Then in step 414, the system searches the captured photo for concentric ellipses. Note that because of perspective, the concentric circles on the reference marker 1 may not appear exactly elliptical in the captured photo. However, any ring-like object which meets a set of predefined criteria for a shape that is substantially elliptical, will be accepted in step 414. An idealized ellipse will be fit to the detected shape, and the idealized ellipse is used henceforth as the "detected" ellipse. Additionally, ellipses are considered herein as being "concentric" if their centerpoints are within a predetermined distance from each other.

Figure 5:
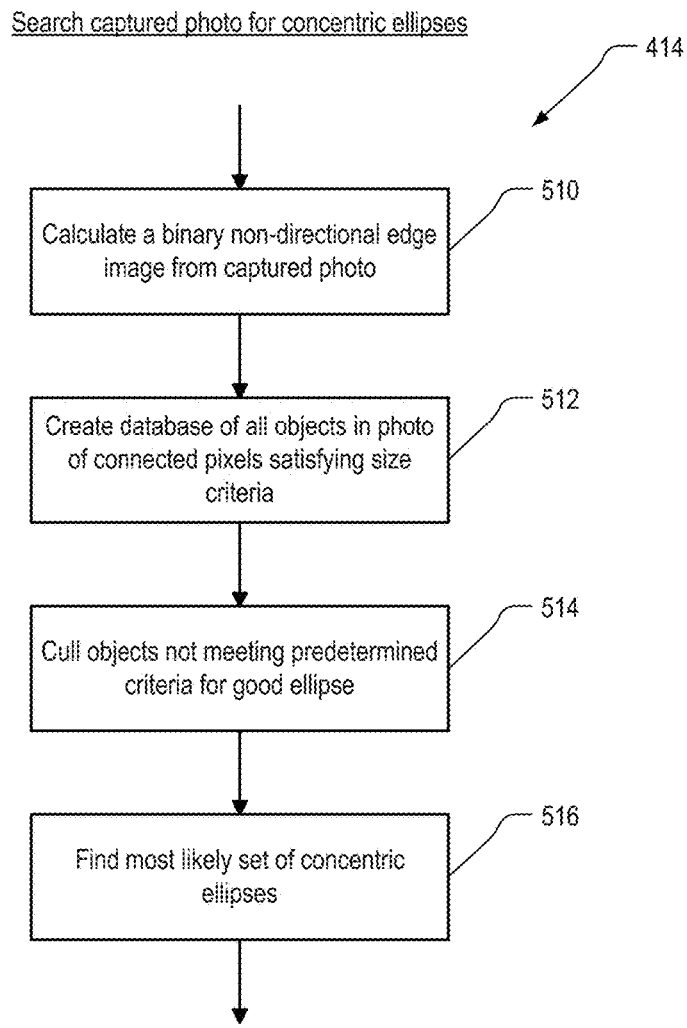

FIG. 5 is a flowchart detail of the step 414 FIG. 4. Optionally, before the steps in FIG. 5 begin, the system may smooth the image to reduce any noise, as well as reduce it to grayscale. Smoothing may be accomplished using the ImageJ "Smooth" function, and reduction to grayscale may be accomplished using the ImageJ "8-bit" function. Then in step 510, the system calculates a binary non-directional edge image from the captured photograph. This may be accomplished by using the ImageJ "Find Edges" function to high-pass-filter the image non-directionally, and the ImageJ "Make Binary" function to threshold the image.

Figure 6:
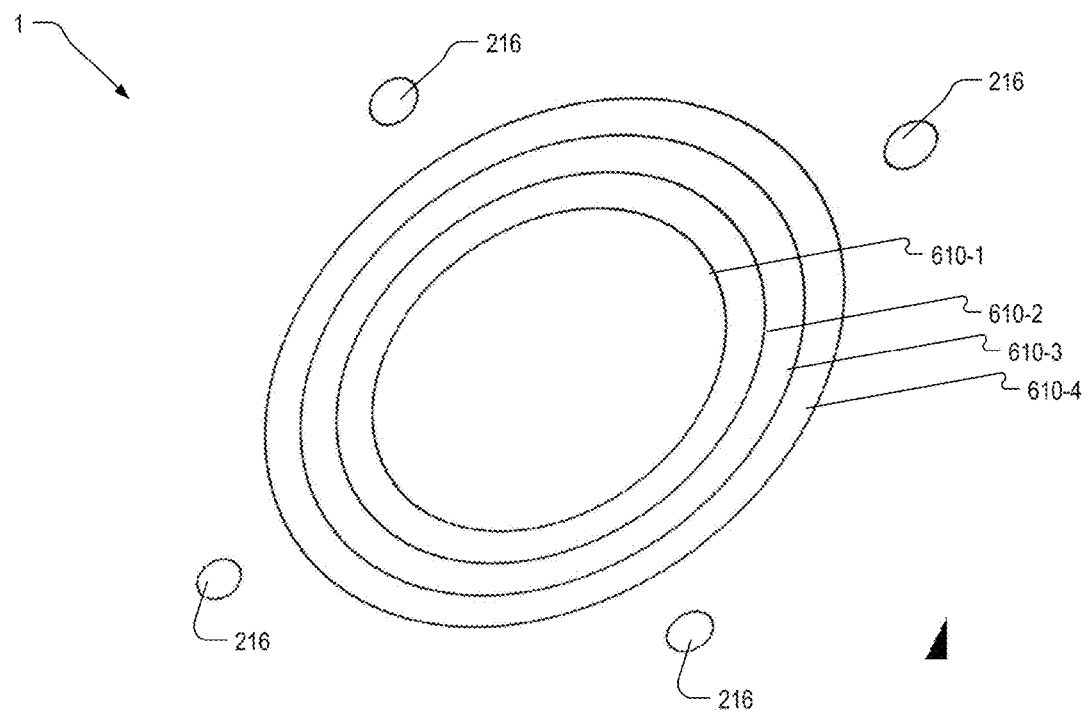
FIG. 6 illustrates an edge image created from elliptical rings in FIG. 3.

FIG. 6 illustrates the edge image created in step 510 from the elliptical rings 210 and 212 in the captured photograph as illustrated in FIG. 3. It can be seen that the rings now appear as a set of four concentric elliptical lines 610-1, 610-2, 610-3 and 610-4 (representatively 610). In some photographs in which the concentric rings of FIG. 3 are not distinct, not all four lines 610 as shown in FIG. 6 will appear, or some might not form closed loops. The system is configured such that only three of the concentric ellipses need be detected; but if fewer than three or detected, then the set of ellipses is rejected due to low confidence that the location marking has been found. The two concentric rings 210 and 212 are chosen as the location markings in the present embodiment in the embodiment of FIGS. 2 and 3 because they tend to distinguish well from other circular or elliptical features that might be present in the environment and captured in the photograph. For example, a washer captured in a photograph would appear with only two concentric lines in its corresponding edge image: an outer ellipse and an inner ellipse. Most other random features in the captured photograph are also likely to be distinguishable from the dual concentric ring structure of FIGS. 2 and 3.

Note that whereas the reference marker 1 as illustrated in FIG. 2 contains only two concentric rings, another embodiment could include 3 or more concentric rings. A reference marker with three concentric rings would appear as six concentric ellipses in the edge image, and preferably the embodiment requires detection of a group of at least five of them to be detected in order to have sufficient confidence that the detected ellipses correspond to the circles on the reference marker 1. In general, if the reference marker has N concentric circular rings, it is preferred that an embodiment reject a group of detected concentric elliptical lines having fewer than 2N−1 concentric elliptical lines.

As used herein, the term "ring" connotes some line thickness such as is shown in FIGS. 2 and 3, whereas the words "circle" and "ellipse" do not necessarily connote a line thickness. Thus the term "ellipse" includes both an elliptical "ring" such as in FIG. 3, as well as an elliptical line such as in FIG. 6.

In step 512, the system creates a database of all objects in the photograph of connected pixels which satisfy predetermined size criteria. The particle tracker function in ImageJ can be used for this purpose. In particular, this step can involve finding all connected components of the image, where a connected component is one in which at least two pixels are connected by black; and then discarding all objects which have fewer than a predetermined minimum number of pixels or more than a predetermined maximum number of pixels. For example, the minimum and maximum numbers of pixels may be 500 and 100000, respectively, in one embodiment. The database 124 are stored on one or more non-transitory computer readable media. As used herein, the term "database" does not necessarily imply any unity of structure. For example, two or more separate databases, when considered together, still constitute a "database" as that term is used herein.

In step 514, the system culls all objects in the database which do not meet predetermined criteria for a good ellipse. This can involve first attempting to fit an ellipse to each of the objects in the database, and then culling each ellipse in which the length of one of the axes is too large or too small, or the ratio of lengths of the major and minor axes is either too large or too small. Step 514 is useful because if an ellipse is too distorted then it is probably not from the reference marker 1, or if it is from the reference marker 1, then it suggests that the photograph may not have sufficient quality for use in accurately determining the length of the subject feature.

In step 516, the system finds the set of concentric ellipses, from among those remaining in the database, that are most likely to be from the reference marker 1. This can involve calculating the centerpoint of each of the ellipses, grouping together those having the same centerpoint or substantially the same centerpoint, and then finding the group containing the largest number of ellipses. This is the group which is most likely to be from the reference marker 1.

Returning to FIG. 4, after the most likely group of concentric ellipses in the photo has been identified, in step 416 the system determines whether this group contains at least three ellipses. As illustrated in FIG. 6 the edge image of a photo capture of the reference marker 1 should have four concentric ellipses. However, in the embodiment of FIG. 4, a group of three is sufficient to be accepted as being the desired location marking. If the group contains fewer than three ellipses, then in step 418 the photo is rejected and the user may be instructed to snap another. In another embodiment, the system may reject the photo if the group contains fewer than all four ellipses.

In step 420, once the location markings of the reference marker have been identified, the system uses the location of these markings to search for the registration markings 216. As used herein, the "location" of a circle or ellipse in a photo or image, refers to the location of its centerpoint in the photo or image. The location can be represented in a number of different ways in different embodiments. For an ellipse, for example, the location can be represented for example by its two foci, or by the endpoints of one of its axes, or by the actual centerpoint of the ellipse. Other representations will be apparent to the reader. "Determination" of the location of a circle or ellipse, as used herein, occurs when the location is identified for sufficient features to identify the location of the centerpoint. The term, as used herein, does not require determination of the actual centerpoint.

Figure 7:
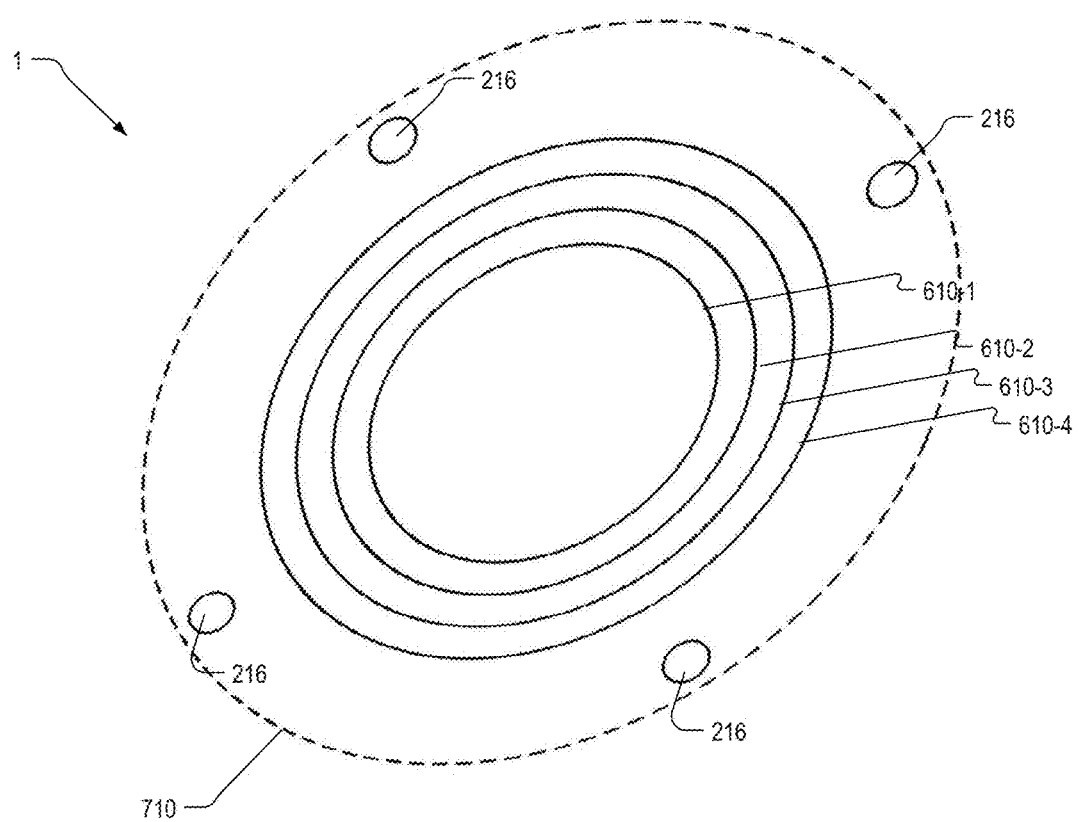
FIG. 7 illustrates a search boundary for searching for registration markings.

The search in step 420 is limited to a predefined maximum distance from the location markings. Preferably, the search region is bounded on the outside by an ellipse which is concentric with the outer ellipse of the detected location markings, and whose major axis coincides with the major axis of one of the detected ellipses and is larger than the major axis of the outer detected ellipse by a predetermined percentage, for example 10%. FIG. 7 illustrates such a search boundary with the broken line ellipse 710. Preferably, the search region is also bounded in the inside by the outermost one of the detected ellipses 610.

Figure 8:
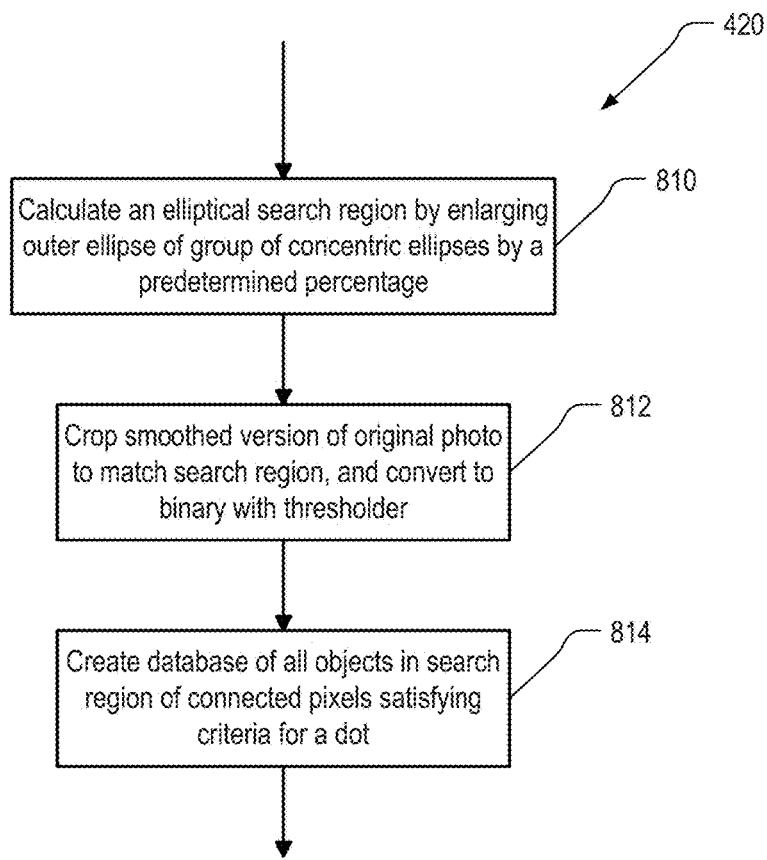

FIG. 8 is a flow chart detail of step 420. In step 810, the system calculates an elliptical search region by enlarging the outermost ellipse of the detected group of concentric ellipses, by the predetermined percentage. In step 812, the system returns to the original photograph after smoothing, and either thresholds only the search region or thresholds the entire image and crops all but the search region. The ImageJ "Make Binary" function can be used for thresholding and the ImageJ OvalRoi library function can be used for cropping. In another embodiment, the cropping can crop out only the region outside the search boundary 710, and the system merely rejects any objects found within the outermost detected ellipse. In step 814, the system creates a database of all objects in the search region of connected pixels satisfying predetermined criteria for the likely shape and size of one of the registration markings 216. In the case of a dot, as in FIG. 2, these criteria might require a predefined minimum and maximum size, and a circularity which is better than a predetermined value. The Particle Tracker ImageJ function can again be used for this purpose. Again, a circular dot is chosen for the registration markings because it is rotationally agnostic. However, other shapes can work instead, with appropriate adaptations.

Returning again to FIG. 4, after likely registration markings have been detected within the search region, in step 422 the system determines whether the number of registration markings detected in the search region is equal to four. If not, then in step 424 the photo is rejected and the user may be instructed to snap another. In another embodiment, the system may instead return to step 414 to try the next-best group of detected concentric ellipses. Also, in an embodiment in which the registration markings identify vertices of a regular polygon with more than four vertices, step 422 may determine whether the number of registration makings detected in the search region is greater than four.

In step 426, using the detected positions of the four registration markings in the captured photo, the system determines what the pose was of the reference marker 1 relative to the camera 3 when the photo was snapped. As used herein, the orientation of an object relative to a camera is referred herein to as the "pose" of the object. This definition may differ from usages of the term by others, in which the term is sometimes used to refer to the orientation of an object in combination with its position (distance and/or translation) relative to the camera. It will be appreciated that the "pose" of an object relative to the camera may be represented internally in the computer system as the geometrical transformation which will convert the pose of an object in a photo to match a predetermined pose (such as one in which the camera is aimed directly perpendicular to the plane of the object). It will be seen that in an embodiment described herein, the pose of the reference marker relative to the camera is represented by eight values: the positions of the four registration dots in the captured photo, and the positions of the same four dots in the desired transformed image.

Figure 9:
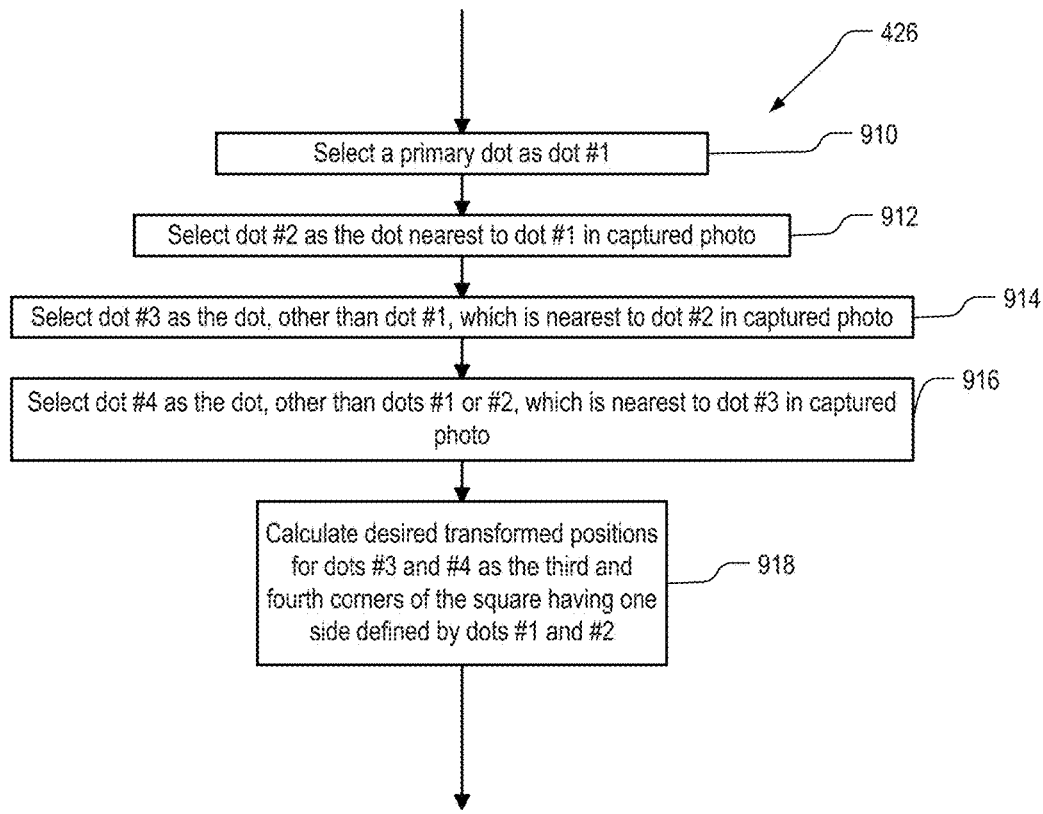

FIG. 9 is a flow chart detail of step 426 in FIG. 4. In order to determine the pose, a transformation is calculated from the positions of the vertices indicated by the four dots detected in the photo, to the positions of the vertices of a square having one side that is the same as one side of a polygon indicated by the four dots detected in the photo. Thus in step 910, any one dot detected in the photo is selected as "dot #1", the "primary" dot. For example, the dot having the minimum x-coordinate may be selected. In step 912, the dot nearest dot #1 in the captured photo is selected as dot #2. Since dot #2 is closer to dot #1 than any of the other detected dots, it is known that these two dots are endpoints of an edge of the polygon. In step 914, the dot, other dot #1, which is nearest to dot #2 in the captured photo, is selected as dot #3. Thus dots 2 and 3 must identify a second side of the polygon, adjacent to the first side. In step 916, the dot, other dots #1 and #2, which is nearest to dot #3 in the captured photo, is selected as dot #4. Steps 910, 912, 914 and 916 therefore together yield the positions of the dots sequentially around the polygon defined by the four dots as captured. Finally, in step 918, the system calculates the desired transformed positions for dots #3 and #4 as the third and fourth corners of a square having one side defined by dots #1 and #2. In particular, if $(x_a, y_a)$ and $(x_b, y_b)$ are the pixel positions of two adjacent dots bounding the longest edge of the polygon, we first determine the relative rotation angle $\alpha$ of this edge with respect to the photo horizontal edge. Then for each of the dots (x,y) we compute the desired position (x',y') of its corresponding target position according to:

$$x'=(x-x_c)*\cos(\alpha)-(y-y_c)*\sin(\alpha)+x_c+x_0$$

$$y'=(x-x_c)*\sin(\alpha)+(y-y_c)*\cos(a)+y_c+y_0$$

where $(x_c, y_c)$ is the rotational center point of the square in the original photo, and $(x_0, y_0)$ is the top left corner point of the photo.

The pose, then, is indicated by the positions of the four dots in the captured photograph, in conjunction with the positions of the four dots in their transformed positions. In the embodiment of FIG. 9, the transformed positions for dots #1 and #2 are the same as their locations as detected in the photo. In another embodiment, transformed positions for dots #1 and/or #2 can be different.

As used herein, two items are "adjacent" to each other if they are not separated by another item of the same type. For example, two dots of the registration marking are considered "adjacent" to each other if there is no intervening dot between them when proceeding around the polygon, even though the two dots do not touch each other.

Returning again to FIG. 4, after the pose has been determined, in step 428 the original captured photograph is transformed based on the pose. This step can be accomplished by providing the original captured photo, together with the original and desired positions of the four dots, to any known or future-developed homographic transformation functions, such as one based on the algorithms described in Wilhelm Burger et al., "Digital Image Processing, An Algorithmic Introduction using Java", Chapter 21, Section 21.1.4, "Projective (Four-Point) Mapping" (2016) [First Published in 2008]. The entire Burger book is incorporated by reference herein, since many of the individual image processing functions referred to herein are explained in that book. See also David Eberly, Geometric Tools, LLC, "Perspective Mappings" (2012), available online at geometrictools(dot)com/Documentation/PerspectiveMappings.pdf, also incorporated herein by reference.

The resulting transformed image now contains the captured photo as if the camera had been disposed directly over and oriented orthogonally to the reference marker when the photo was snapped. By transforming the entire image based on the pose, the captured subject feature 2 is also transformed in the same way. The transformation of the subject feature 2 is sufficiently accurate so long as it is relatively close to the reference marker 1 and substantially coplanar with it. In another embodiment, only the portion of the captured photo containing the subject feature 2 need be transformed based on the pose.

Note that in step 426, the distance (in pixels) between any two adjacent ones of the dots in the transformed image also indicates the scale of the captured photo, because the actual distance between them on the reference marker 1 itself is known. In particular, if the center-to-center distance between two adjacent dots on the reference marker 1 is L, then the scale of the captured photo in units of length per pixel is given by L/(number of pixels encompassed by any side of the transformed square).

Note also that a different embodiment could also use this information to re-size the image to a desired scale for output, merely by calculating a transformed position for dot #2 in step 918 that is the desired distance from dot #1, prior to calculating desired transformed positions for dots #3 and #4. That would obviate any need to report scale with the output transformed image. An embodiment could also use this opportunity to rotate the image in-plane to some desired rotation. Both of these additional transformations can be accomplished merely by calculating desired positions for three of the dots, or even for all four, and providing them to the ImageJ "Rotate Image" and "Resize" functions in step 428.

In step 430, the transformed image and (at least if the image hasn't been transformed to a standard scale) an indication of scale in the transformed image, are output for measurement of the size of the subject feature. Scale can be indicated for example in units of millimeters/pixel. In one embodiment, a known DICOM format can be used to output this information, and to input it into DICOM imaging software. DICOM (Digital Imaging and Communications in Medicine) is a communications standard managed by the Medical Imaging & Technology Alliance. Information on DICOM is well known and can be found, for example, at dicom.nema.org/standard.html, incorporated by reference herein. In DICOM, scale can be indicated by metadata accompanying the image. In another embodiment, scale can be indicated by superimposing a caliper into the transformed image itself. Other ways of indicating scale will be apparent to the reader. In step 432, a user, such as a clinician at a different location, estimates the desired size measurement of the subject feature from the transformed version of the captured photo.

It can be seen that the combination of concentric circular rings plus registration dots identifying vertices of a regular polygon, within a known and expected region near the concentric rings, is both easy to detect in a variety of difficult photographic conditions and also can provide excellent confidence that what is detected is in fact the reference marker 1. Other aspects of the method as described herein, such as detecting elliptical edges of the rings rather than the rings themselves, can further improve the effectiveness of the process.

Figure 10:
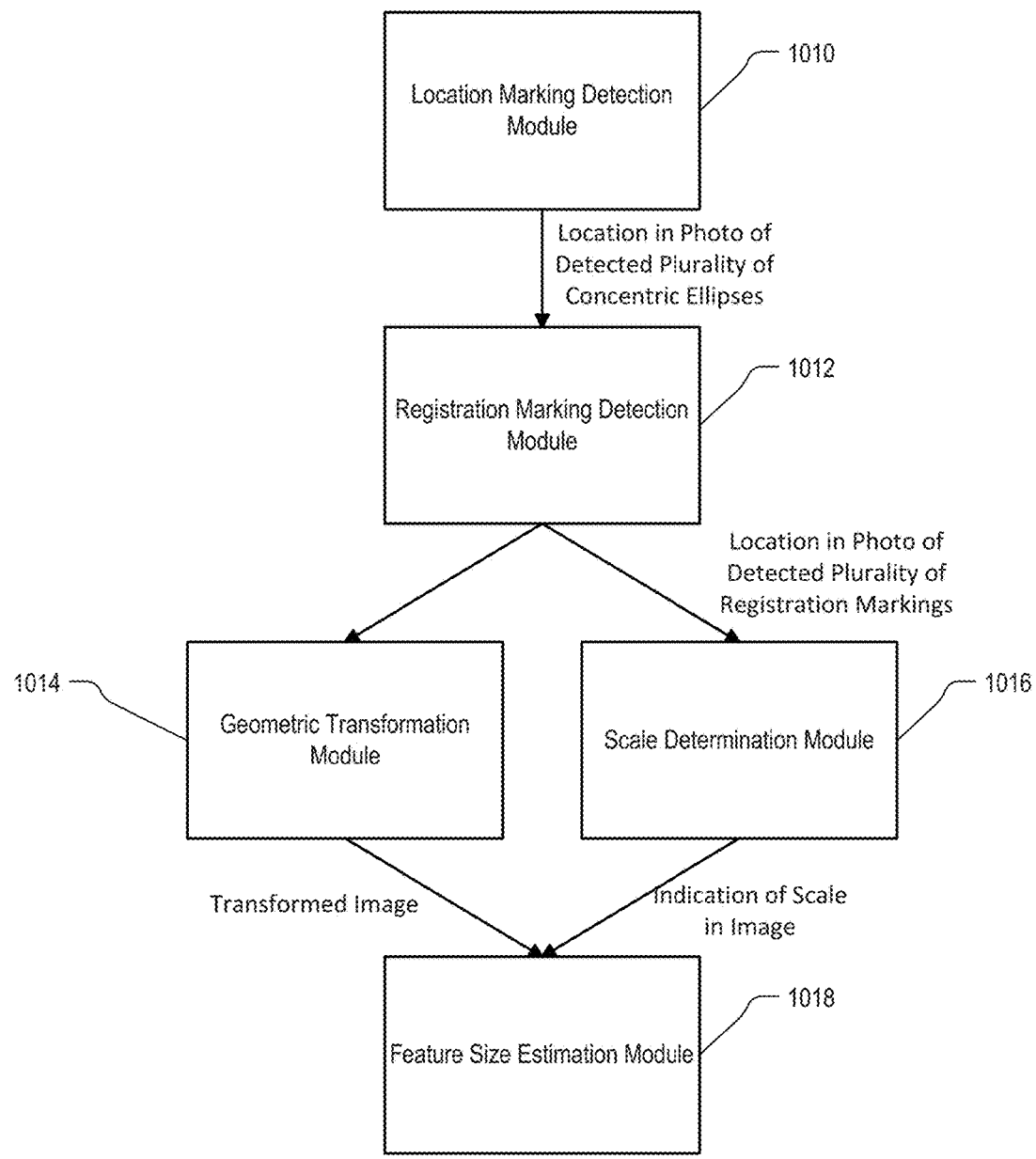
FIG. 10 illustrates an embodiment using modules.

FIG. 10 is an illustration of an embodiment of the invention in which major aspects of the method are performed by individual modules. Referring to FIG. 10, Location Marking Detection Module 1010 takes the captured photo as input, and detects the location in photo of a detected plurality of concentric ellipses which is most likely to be a captured version of the circular reference marker rings in FIG. 2. Location Marking Detection Module 1010, for example, can perform steps 414 and 416 of FIG. 4.

Location Marking Detection Module 1010 outputs this information to Registration Marking Detection Module 1012, which finds the registration markings 216. Registration Marking Detection Module 1012, for example, can perform steps 420 and 422 of FIG. 4.

Registration Marking Detection Module 1012 outputs the location in the photo of detected plurality of registration markings, to a Geometric Transformation Module 1014, which transforms the original captured photo (or at least the subject feature in the photo) as needed such that the registration markings are located at respective vertices of a regular polygon corresponding to the one on the reference marker. Geometric Transformation Module 1014, for example, can perform steps 426 and 428 of FIG. 4.

In some embodiments, Registration Marking Detection Module 1012 outputs the location in the photo of the detected plurality of registration markings, also to a Scale Determination Module 1016, which determines the scale of the transformed image based on the distance between two of the detected registration markings. For example, Scale Determination Module 1016 can use the techniques described above for determining the scale.

Geometric Transformation Module 1014 and, in an embodiment in which it exists, Scale Determination Module 1016, output the transformed image and the scale indication, respectively, to a Feature Size Estimation Module 1018. The Feature Size Estimation Module 1018 measures the size of a desired aspect of the subject feature 2 as it appears in the transformed image, and converts it to a real world measurement using the scale indication.

In one embodiment, one or more, or all, of the modules in FIG. 10 is implemented in hardware. In another embodiment, one or more of the modules is implemented in software running on a special purpose or general purpose computer. In either embodiment the modules can be implemented on the mobile device 3 (FIG. 1) or on a separate unit to which the captured photo is transmitted.

Figure 11:
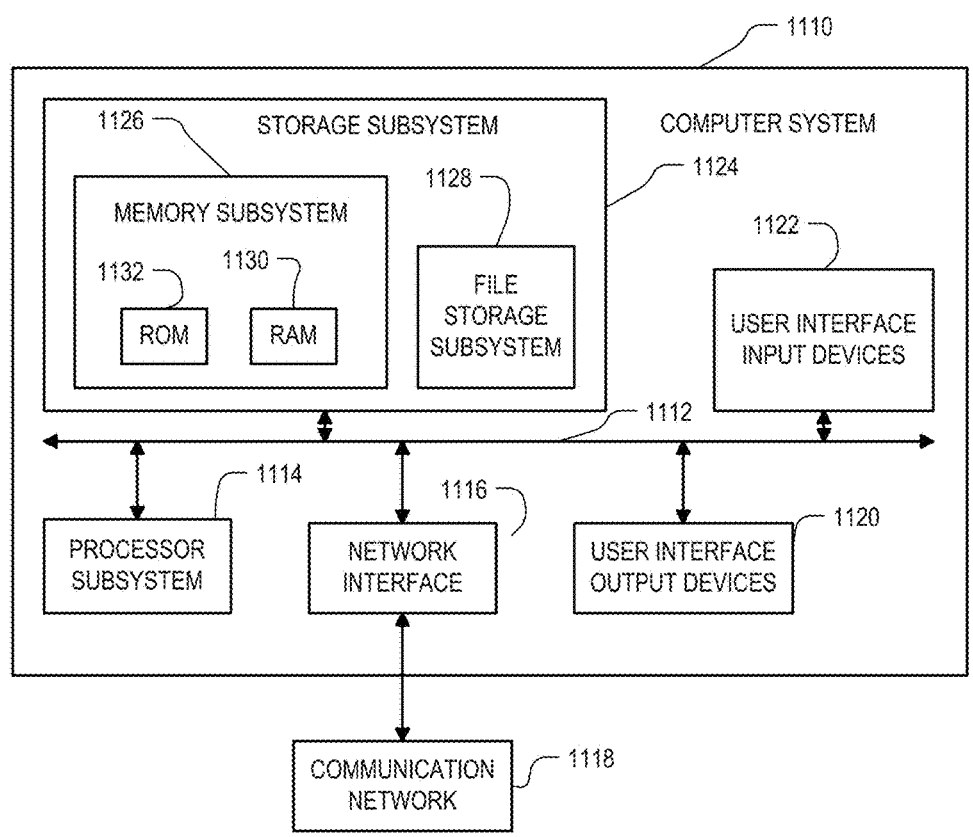
FIG. 11 is a simplified block diagram of a computer system that can be used to implement aspects of the invention.

FIG. 11 is a simplified block diagram of a computer system 1110 that can be used to implement aspects of the present invention. While FIGS. 4, 5, 8 and 9 indicate individual acts carrying out specified operations, it will be appreciated that each act actually causes the computer system 1110 to operate in the specified manner.

Computer system 1110 typically includes a processor subsystem 1114 which communicates with a number of peripheral devices via bus subsystem 1112. These peripheral devices may include a storage subsystem 1124, comprising a memory subsystem 1126 and a file storage subsystem 1128, user interface input devices 1122, user interface output devices 1120, and a network interface subsystem 1116. The input and output devices allow user interaction with computer system 1110. Network interface subsystem 1116 provides an interface to outside networks, including an interface to communication network 1118, and is coupled via communication network 1118 to corresponding interface devices in other computer systems. Communication network 1118 may comprise many interconnected computer systems and communication links. These communication links may be wireline links, optical links, wireless links, or any other mechanisms for communication of information. While in one embodiment, communication network 1118 is the Internet, in other embodiments, communication network 1118 may be a WiFi link, a Bluetooth link, a cellular link, a wireline link, or any suitable network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 1122 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 1110 or onto computer network 1118.

User interface output devices 1120 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 1110 to the user or to another machine or computer system.

Storage subsystem 1124 stores the basic programming and data constructs that provide the functionality of certain embodiments of the present invention. For example, in embodiments in which the various modules implementing the functionality of certain embodiments of the invention involve software, such software may be stored in storage subsystem 1124. These software modules are generally executed by processor subsystem 1114.

Memory subsystem 1126 typically includes a number of memories including a main random access memory (RAM) 1130 for storage of instructions and data during program execution and a read only memory (ROM) 1132 in which fixed instructions are stored. File storage subsystem 1128 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 1128. The host memory 1126 contains, among other things, computer instructions which, when executed by the processor subsystem 1114, cause the computer system to operate or perform functions as described herein. As used herein, processes and software that are said to run in or on "the host" or "the computer", execute on the processor subsystem 1114 in response to computer instructions and data in the host memory subsystem 1126 including any other local or remote storage for such instructions and data.

Bus subsystem 1112 provides a mechanism for letting the various components and subsystems of computer system 1110 communicate with each other as intended. Although bus subsystem 1112 is shown schematically as a single bus, alternative embodiments of the bus subsystem may use multiple busses.

Computer system 1110 itself can be of varying types including a personal computer, a portable computer, a mobile phone, a workstation, a computer terminal, a network computer, a television, a mainframe, a server farm, or any other data processing system or user device. Due to the ever-changing nature of computers and networks, the description of computer system 1110 depicted in FIG. 11 is intended only as a specific example for purposes of illustrating some embodiments of the present invention. Many other configurations of computer system 1110 are possible having more or less components than the computer system depicted in FIG. 11.

Figure 12:
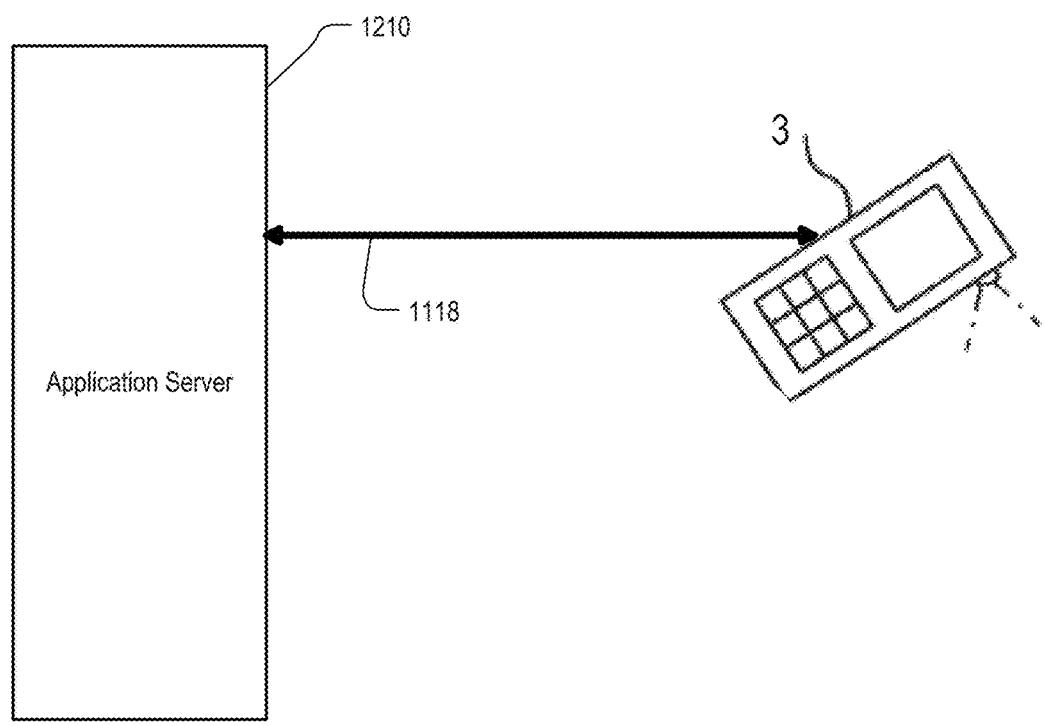
FIG. 12 illustrates an arrangement by which an application server transmits software to a mobile device to implement aspects of the invention.

In embodiments in which some or all of the operations described herein are implemented in software, a version of the software may be housed on a server separate from the mobile device 3. FIG. 12 illustrates such an arrangement. FIG. 12 illustrates the mobile device 3, and an application server 1210. Upon request from the mobile device 3, the application server 1210 transmits the software to the mobile device 3 via Communication network 1118.

As used herein, a given value is "responsive" to a predecessor value if the predecessor value influenced the given value. If there is an intervening processing element, step or time period, the given value can still be "responsive" to the predecessor value. If the intervening processing element or step combines more than one value, the signal output of the processing element or step is considered "responsive" to each of the value inputs. If the given value is the same as the predecessor value, this is merely a degenerate case in which the given value is still considered to be "responsive" to the predecessor value. "Dependency" of a given value upon another value is defined similarly.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "indicate" is used herein to mean the same as "identify".

The applicant hereby discloses in isolation each individual feature described herein and any combination of two or more such features, to the extent that such features or combinations are capable of being carried out based on the present specification as a whole in light of the common general knowledge of a person skilled in the art, irrespective of whether such features or combinations of features solve any problems disclosed herein, and without limitation to the scope of the claims. The applicant indicates that aspects of the present invention may consist of any such feature or combination of features. In view of the foregoing description it will be evident to a person skilled in the art that various modifications may be made within the scope of the invention.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. In particular, and without limitation, any and all variations described, suggested or incorporated by reference in the Background section of this patent application are specifically incorporated by reference into the description herein of embodiments of the invention. In addition, any and all variations described, suggested or incorporated by reference herein with respect to any one embodiment are also to be considered taught with respect to all other embodiments. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A method for estimating a size measurement of a subject feature on a body, for use with a photo, snapped by a camera and containing both the subject feature and a reference marker, the method comprising:
   detecting in the captured photo a location of a plurality of concentric ellipses corresponding to a plurality of concentric circles in the reference marker, the plurality of concentric circles including an outer circle, the reference marker further having registration markings located outside the outer circle but within a predetermined region relative to the plurality of concentric circles, the registration markings identifying the vertices of a regular polygon having at least four sides;
   detecting the registration markings in the captured photo within a predetermined region which is outside an outer one of the concentric ellipses in the captured photo;
   geometrically transforming at least the subject feature in the photo in dependence upon the locations in the captured photo of at least first, second, third and fourth vertices of the polygon as identified by the registration markings; and
   providing the transformed image for the size measurement.

2. The method of claim 1, further comprising providing, for the size measurement and in association with the transformed image, an indication of scale of the reference marker in the transformed image.

3. The method of claim 1, wherein the plurality of concentric circles consists of N>1 concentric circular rings each having a thickness, and wherein detecting a plurality of concentric ellipses comprises:
   forming a non-directional edge image in dependence upon the captured photo; and
   detecting in the edge image a set of at least 2N−1 concentric elliptically shaped edges.

4. The method of claim 1, wherein the plurality of concentric circles comprises two concentric circular rings each having a thickness, and wherein detecting a plurality of concentric ellipses comprises:
   forming a non-directional edge image in dependence upon the captured photo; and
   detecting in the edge image a set of at least three concentric elliptically shaped edges.

5. The method of claim 1, wherein detecting the registration markings comprises searching for the registration markings only within the predetermined region outside the outer one of the concentric ellipses in the captured photo.

6. The method of claim 1, wherein the predetermined region extends outside the outer one of the concentric ellipses to an elliptical search boundary which is concentric with one of the detected ellipses in the captured photo, and wherein detecting the registration markings comprises:
   determining the elliptical search boundary in dependence upon a size of one of the detected concentric ellipses in the captured photo; and
   searching for the registration markings only within the predetermined region and outside the outer one of the concentric ellipses in the captured photo.

7. The method of claim 1, wherein geometrically transforming comprises:
   in dependence upon locations in the captured photo of first and second ones of the vertices of the polygon as identified by the registration markings, calculating transformed positions for at least the first, second, third and fourth vertices of the polygon such that the locations of the first and second vertices in the captured photo, together with the calculated transformed positions of the third and fourth vertices, form four vertices of a regular polygon; and
   transforming at least the subject feature in dependence upon the locations in the captured photo, and the transformed positions of, the first, second, third and fourth vertices.

8. The method of claim 7, wherein the first and second vertices are the endpoints of a first side of the polygon as identified by the registration markings, and wherein calculating transformed positions for at least the first, second, third and fourth vertices of the polygon comprises:
   determining the transformed position for the first and second vertices as the same as the locations in the captured photo of respectively the first and second vertices; and
   determining the transformed positions for the third and fourth vertices as third and fourth vertices of a regular polygon having the first side as one of its sides.

9. The method of claim 7, wherein providing the transformed image in association with an indication of scale comprises calculating the scale in dependence upon the distance in the captured photo between the first and second vertices.

10. The method of claim 1, wherein the indication of scale is an indication of unit length in the reference marker which corresponds to a pixel in the transformed image.

11. The method of claim 1, wherein providing for the size measurement comprises adding a ruler to the transformed image, the ruler indicating a length in the reference marker which corresponds to length in the transformed image as specified on the ruler.

12. The method of claim 1, wherein geometrically transforming at least the subject feature in the photo comprises geometrically transforming the entire photo.

13. The method of claim 1, wherein a particular one of the registration markings in the reference marker is a circle, and wherein the vertex identified by the particular registration marking is the centerpoint of the particular registration marking.

14. The method of claim 1, wherein the regular polygon is a square.

15. The method of claim 1, further comprising placing the reference marker on the body and snapping the photo.

16. The method of claim 1, further comprising estimating the size measurement in dependence upon the transformed image and the indication of scale.

17. A system for estimating a size measurement of a subject feature on a body, for use with a photo, snapped by a camera and containing both the subject feature and a reference marker, the system comprising:
    a location marking detection module which detects in the captured photo a location of a plurality of concentric ellipses corresponding to a plurality of concentric circles in the reference marker, the plurality of concentric circles including an outer circle, the reference marker further having registration markings located outside the outer circle but within a predetermined region relative to the plurality of concentric circles, the registration markings identifying the vertices of a regular polygon having at least four sides;
    a registration marking detection module which searches for the registration markings in the captured photo only within a predetermined region which is outside an outer one of the concentric ellipses in the captured photo; and
    a geometric transformation module which transforms at least the subject feature in the photo in dependence upon the locations in the captured photo of at least first, second, third and fourth vertices of the polygon as identified by registration markings detected by the registration marking detection module,
    the system further providing the transformed image for the size measurement.

18. A computer readable medium having stored thereon in a non-transitory manner, a plurality of software code portions defining logic for estimating a size measurement of a subject feature on a body, for use with a photo, snapped by a camera and containing both the subject feature and a reference marker, including logic for:
    detecting in the captured photo a location of a plurality of concentric ellipses corresponding to a plurality of concentric circles in the reference marker, the plurality of concentric circles including an outer circle, the reference marker further having registration markings located outside the outer circle but within a predetermined region relative to the plurality of concentric circles, the registration markings identifying the vertices of a regular polygon having at least four sides;
    detecting the registration markings in the captured photo within a predetermined region which is outside an outer one of the concentric ellipses in the captured photo;
    geometrically transforming at least the subject feature in the photo in dependence upon the locations in the captured photo of at least first, second, third and fourth vertices of the polygon as identified by the registration markings; and
    providing the transformed image for the size measurement.

19. A method, for use with a mobile device having a processor and a memory to store software instructions which are executable by the processor, comprising:
    providing a plurality of software code portions which define logic for estimating a size measurement of a subject feature on a body, for use with a photo, snapped by a camera and containing both the subject feature and a reference marker, the code portions defining logic for:
        detecting in the captured photo a location of a plurality of concentric ellipses corresponding to a plurality of concentric circles in the reference marker, the plurality of concentric circles including an outer circle, the reference marker further having registration markings located outside the outer circle but within a predetermined region relative to the plurality of concentric circles, the registration markings identifying the vertices of a regular polygon having at least four sides,
        detecting the registration markings in the captured photo within a predetermined region which is outside an outer one of the concentric ellipses in the captured photo,
        geometrically transforming at least the subject feature in the photo in dependence upon the locations in the captured photo of at least first, second, third and fourth vertices of the polygon as identified by the registration markings, and
        providing the transformed image for the size measurement; and
    transmitting the code portions toward the mobile device.

\* \* \* \* \*